(12) United States Patent
Marthandam et al.

(10) Patent No.: US 11,953,452 B2
(45) Date of Patent: Apr. 9, 2024

(54) IONIZING RADIATION DETECTOR WITH REDUCED STREET WIDTH AND IMPROVED COUNT RATE STABILITY

(71) Applicant: REDLEN TECHNOLOGIES, INC., Saanichton (CA)

(72) Inventors: Pramodha Marthandam, Victoria (CA); Michael Kevin Jackson, Victoria (CA)

(73) Assignee: REDLEN TECHNOLOGIES, INC., Saanichton (CA)

( * ) Notice: Subject to any disclaimer, the term of this patent is extended or adjusted under 35 U.S.C. 154(b) by 261 days.

(21) Appl. No.: 17/562,288

(22) Filed: Dec. 27, 2021

(65) Prior Publication Data

US 2022/0276184 A1 Sep. 1, 2022

Related U.S. Application Data

(60) Provisional application No. 63/154,969, filed on Mar. 1, 2021.

(51) Int. Cl.
| | | |
|---|---|---|
| *G01N 23/046* | (2018.01) | |
| *A61B 6/00* | (2006.01) | |
| *A61B 6/03* | (2006.01) | |
| *A61B 6/42* | (2024.01) | |

(Continued)

(52) U.S. Cl.
CPC ........... *G01N 23/046* (2013.01); *A61B 6/032* (2013.01); *A61B 6/035* (2013.01); *A61B 6/4233* (2013.01); *A61B 6/4241* (2013.01); *G01T 1/17* (2013.01); *G01T 1/241* (2013.01); *G01N 2223/501* (2013.01)

(58) Field of Classification Search
CPC ....... A61B 6/032; A61B 6/035; A61B 6/4233; A61B 6/4241; G01N 23/046; G01N 2223/501; G01T 1/17; G01T 1/241
See application file for complete search history.

(56) References Cited

U.S. PATENT DOCUMENTS

| | | | | |
|---|---|---|---|---|
| 5,500,534 A | * | 3/1996 | Robinson | ................ G01T 1/185 |
| | | | | 250/374 |
| 6,362,484 B1 | * | 3/2002 | Beyne | ..................... H01J 47/02 |
| | | | | 250/374 |
| 9,847,369 B2 | | 12/2017 | El-Hanany et al. | |

(Continued)

OTHER PUBLICATIONS

U.S. Appl. No. 17/019,750, filed Sep. 14, 2020, Redlen Technologies, Inc.

(Continued)

*Primary Examiner* — Blake C Riddick
(74) *Attorney, Agent, or Firm* — THE MARBURY LAW GROUP PLLC

(57) ABSTRACT

An ionizing radiation detector, such as a photon counting computed tomography detector, includes a semiconductor material plate, a plurality of anodes located on a first side of the semiconductor material plate, where the gaps (i.e., streets) between adjacent anodes are less than 15 μm in width, and at least one cathode located on a second side of the semiconductor material plate. Ionizing radiation detectors according to various embodiments may have improved count rate stability (CRS) characteristics and a reduced number of Non-Conforming Pixels (NCPs) relative to conventional detectors.

13 Claims, 4 Drawing Sheets

(51) Int. Cl.
*G01T 1/17* (2006.01)
*G01T 1/24* (2006.01)

(56) References Cited

U.S. PATENT DOCUMENTS

| | | | |
|---|---|---|---|
| 2010/0001191 A1* | 1/2010 | Takahashi | G01T 1/2935 250/361 R |
| 2013/0266114 A1* | 10/2013 | Chen | G01T 1/241 250/371 |
| 2013/0287172 A1* | 10/2013 | Hermann | H01L 27/14643 378/62 |
| 2014/0319363 A1* | 10/2014 | Engel | H01L 27/14659 257/428 |
| 2016/0240584 A1 | 8/2016 | El-Hanany et al. | |
| 2018/0224564 A1* | 8/2018 | Fu | G01T 1/247 |
| 2020/0150297 A1 | 5/2020 | Iniewski et al. | |
| 2020/0367839 A1 | 11/2020 | Iniewski et al. | |
| 2020/0393576 A1 | 12/2020 | Harris et al. | |
| 2021/0022695 A1 | 1/2021 | Iniewski et al. | |
| 2021/0063589 A1 | 3/2021 | Iniewski et al. | |
| 2021/0263172 A1* | 8/2021 | Shimada | G01T 1/242 |

OTHER PUBLICATIONS

U.S. Appl. No. 17/064,089, filed Oct. 6, 2020, Redlen Technologies, Inc.

U.S. Appl. No. 17/193,219, filed Mar. 5, 2021, Redlen Technologies, Inc.

U.S. Appl. No. 17/225,416, filed Apr. 8, 2021, Redlen Technologies, Inc.

U.S. Appl. No. 17/390,426, filed Jul. 30, 2021, Redlen Technologies, Inc.

U.S. Appl. No. 17/395,794, filed Aug. 6, 2021, Redlen Technologies, Inc.

* cited by examiner

IONIZING RADIATION DETECTOR WITH REDUCED STREET WIDTH AND IMPROVED COUNT RATE STABILITY

FIELD

The present application relates generally to ionizing radiation detectors, such as photon counting computed tomography (PCCT) radiation detectors, and to imaging systems using ionizing radiation detectors.

BACKGROUND

In typical photon counting X-ray computed tomography (CT) imaging systems currently in use, the charge cloud resulting from an X-ray photon impinging on a sensor is converted to an amplified voltage by a charge sensitive amplifier (CSA). The voltage output of the CSA is compared against a number of user-settable thresholds. Each threshold level is associated with a counter, such that each counter represents an energy bin representing the energy range between two adjacent thresholds. Such PCCT systems still suffer from imperfect count rate stability.

SUMMARY

According to one embodiment, an ionizing radiation detector includes a semiconductor material plate, a plurality of anodes located on a first side of the semiconductor material plate, where the gaps between adjacent anodes are less than 15 μm in width, and at least one cathode located on a second side of the semiconductor material plate.

Further embodiments relate to photon counting computed tomography (PCCT) systems utilizing an embodiment ionizing radiation detector.

Embodiment ionizing radiation detectors in which the gaps (i.e., "streets") between adjacent anodes are less than 15 μm in width may provide improved count rate stability (CRS) characteristics and a reduced number of Non-Conforming Pixels (NCPs) relative to conventional detectors.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims. Any reference to claim elements in the singular, for example, using the articles "a," "an," or "the" is not to be construed as limiting the element to the singular. The terms "example," "exemplary," or any term of the like are used herein to mean serving as an example, instance, or illustration. Any implementation described herein as an "example" is not necessarily to be construed as preferred or advantageous over another implementation. The drawings are not drawn to scale. Multiple instances of an element may be duplicated where a single instance of the element is illustrated, unless absence of duplication of elements is expressly described or clearly indicated otherwise.

Figure 1:
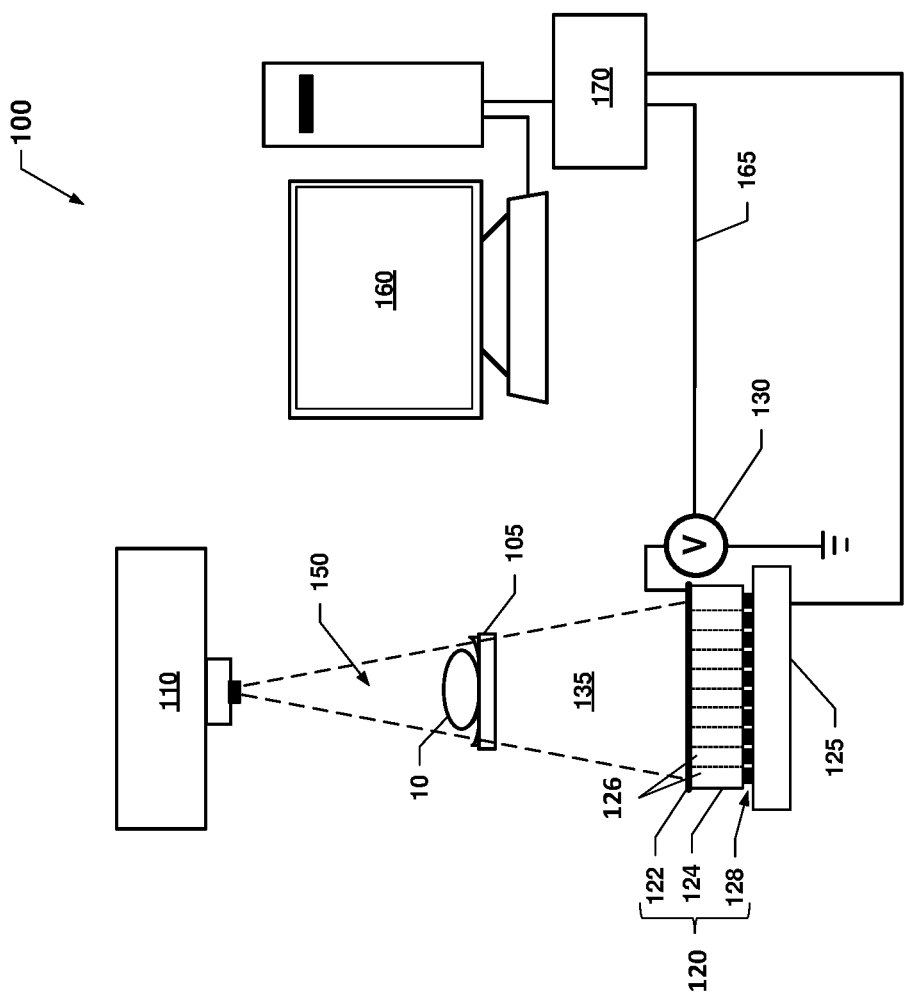
FIG. 1 is a block diagram of an imaging system suitable for use with various embodiments of the present disclosure.

FIG. 1 is a functional block diagram of an example ionizing radiation imaging system in accordance with various embodiments. The illustrated example ionizing radiation imaging system is a CT imaging system 100 that includes an X-ray source 110 (i.e., a source of ionizing radiation), and a radiation detector 120. The CT imaging system 100 may additionally include a support structure 105, such as a table or frame, which may rest on the floor and may support an object 10 to be scanned. The support structure 105 may be stationary (i.e., non-moving) or may be configured to move relative to other elements of the CT imaging system 100. The object 10 may be all or a portion of any biological (e.g., human patient) or non-biological (e.g., luggage) object to be scanned.

The X-ray source 110 is configured to deliver ionizing radiation to the radiation detector 120 by emitting an X-ray beam 135 toward the object 10 and the radiation detector 120. After the X-ray beam 135 is attenuated by the object 10, the beam of radiation 135 is received by the radiation detector 120. The radiation detector 120 includes at least one anode 128 and cathode 122 pair separated by a semiconductor material plate (e.g., semiconductor substrate) 124.

The radiation detector 120 may be controlled by a high voltage bias power supply 130 that selectively creates an electric field between an anode 128 and cathode 122 pair separated by a semiconductor material plate 124. The semiconductor material plate 124 may comprise any suitable X-ray semiconductor material, such as cadmium zinc telluride (i.e., "CdZnTe" or "CZT") or another material, disposed between the anode 128 and cathode 122 and thus configured to be exposed to the electrical field therebetween. For example, there may be a plurality of separate CZT pixels 126 (e.g., 4 to 1024, such as 256 to 864 pixels for example) in the semiconductor material plate 124, each containing and electrically connected to a separate anode 128. One or more cathodes 122 are provided for the plurality of CZT pixels 126. A read-out application specific integrated circuit (ASIC) 125 coupled to the anode(s) 128 and cathode 128 pair may receive signals (e.g., charge or current) from the anode(s) 128 and be configured to provide data to and by controlled by a control unit 170.

The control unit 170 may be configured to synchronize the X-ray source 110, the read-out ASIC 125, and the high voltage bias power supply 130. The control unit 170 may be coupled to and operated from a computing device 160. Alternatively, the computing device 160 and the control unit 170 may be integrated together as one device.

The object 10 may pass between the X-ray source 110 and the radiation detector 120 or alternatively the object may remain stationary while the X-ray source 110 and the radiation detector 120 move relative to the object 10. Either way, the radiation detector 120 may capture incremental cross-sectional profiles of the object 10. The data acquired by the radiation detector 120 may be passed along to the computing device 160 that may be located remotely from the radiation detector 120 via a connection 165. The connection 165 may be any type of wired or wireless connection. If the connection 165 is a wired connection, the connection 165 may include a slip ring electrical connection between any structure supporting the radiation detector 120 and a stationary support part of the support structure 105, which supports any part (e.g., a rotating ring). If the connection 165 is a wireless connection, the radiation detector 120 may contain any suitable wireless transceiver to communicate data with another wireless transceiver that is in communication with the computing device 160. The computing device 160 may include processing and imaging applications that analyze each profile obtained by the radiation detector 120, and a full set of profiles may be compiled to form two-dimensional images of cross-sectional slices of the object 10.

Various alternatives to the design of the CT imaging system 100 of FIG. 1 may be employed to practice embodiments of the present disclosure. CT imaging systems may be designed in various architectures and configurations. For example, a CT imaging system may have a helical architecture. In a helical CT imaging scanner, the X-ray source and detector array are attached to a freely rotating gantry. During a scan, a table (i.e., support structure 105) moves the object 10 smoothly through the scanner creating helical path traced out by the X-ray beam. Slip rings enable the transfer of power and data on and off the rotating gantry. In other embodiments, the CT imaging system may be a tomosynthesis CT imaging system. In a tomosynthesis CT scanner, the gantry may move in a limited rotation angle (e.g., between 15 degrees and 60 degrees) in order to detect a cross-sectional slice of the object. The tomosynthesis CT scanner may be able to acquire slices at different depths and with different thicknesses that may be constructed via image processing. In other embodiments, multiple X-ray sources are disposed at different angles with respect to the detector array. The X-ray sources are turned on sequentially, forming a series of transmission images through the object to be scanned. An image is then reconstructed without requiring any motion of X-ray sources and the detector array.

The detector array of a CT imaging system may include an array of radiation detector elements, referred to herein as pixel detectors. The signals from the pixel detectors may be processed by a pixel detector circuit, which may sort detected photons into energy bins based on the energy of each photon or the voltage generated by the received photon. When an X-ray photon is detected, its energy is determined and the X-ray photon count for its associated energy bin is incremented. For example, if the detected energy of an X-ray photon is 24 kilo-electron-volts (keV), the X-ray photon count for the energy bin of 20-40 keV may be incremented. The number of energy bins may range from one to several, such as two to six. In an illustrative example, an X-ray photon counting detector may have four energy bins: a first bin for detecting photons having an energy between 20 keV and 40 keV, a second bin for detecting photons having an energy between 40 keV and 60 keV, a third bin for detecting photons having an energy between 60 keV and 80 keV, and a fourth bin for detecting photons having an energy above 80 keV. The greater the total number of energy bins, the better the material discrimination.

In CT imaging systems, a scanned object is exposed to an X-ray beam and attenuated photons from the X-ray beam are detected and counted by individual radiation detector pixels in a detector array. When an object (e.g., the object 10) is loaded in a CT imaging system, the X-ray beam may be heavily attenuated, and the number of photons detected by the detector array may be orders of magnitude less than the number of photons emitted from an X-ray source. For image reconstruction purposes, the radiation detector can be exposed to a direct X-ray beam without an intervening object located inside the CT imaging system. In such cases, the X-ray photon count rates in the CT imaging system may reach values of 100 million counts per second per square millimeter (Mcps/mm$^2$) or more. The detector array should be capable of detecting such a wide range of photon count rates.

Figures 2A, 2B:
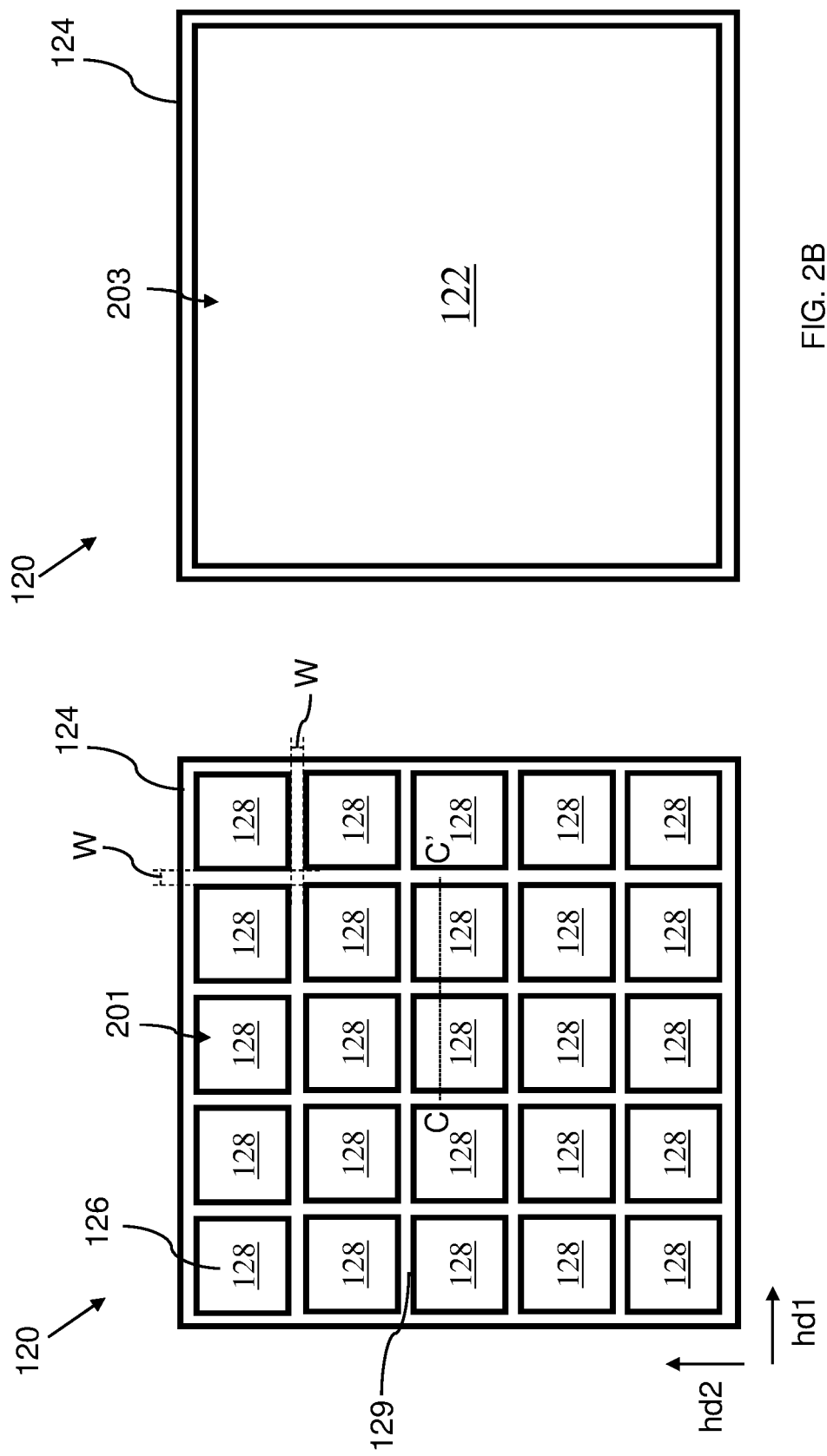
FIGS. 2A and 2B are front and rear views of an ionizing radiation detector according to an embodiment of the present disclosure.
Figure 2C:
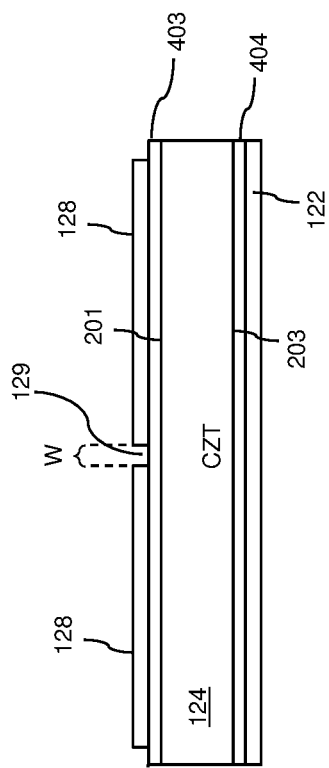
FIG. 2C is a side cross-sectional view of the ionizing radiation detector along plane C-C' in FIG. 2A.

FIGS. 2A-2C schematically illustrate a radiation detector (such as a photon counting computed tomography radiation detector) 120 for an imaging system, such as a CT imaging system 100 as shown in FIG. 1. FIG. 2A illustrates a first (e.g., anode) side 201 of the radiation detector 120, and FIG. 2B illustrates a second (e.g., cathode) side 203 of the radiation detector 120, opposite the first side 201. FIG. 2C illustrates a side cross-sectional view along plane C-C' in FIG. 2A. The radiation detector 120 includes a semiconductor material substrate 124 (e.g., semiconductor wafer), such as a cadmium zinc telluride (CZT) substrate. Anode and cathode electrodes 128, 122 may be located over the semiconductor material substrate 124 on the first 201 and second 203 sides of the detector 120, respectively.

The surfaces of the semiconductor material substrate 124 may be polished and may optionally also be coated with a passivation layer over all or portion(s) of the surfaces of the substrate 124. It is known in the art to prepare surfaces of semiconductors, such as CZT, using various passivation techniques, which can affect the inter-pixel region, the region under the anodes, and the regions under the cathodes. The streets can play a contributing role to instability due to charging of the street surface by photogenerated electrons, which may accumulate and affect later electron paths, in particular, the degree of charge sharing of electrons generated in the voxel regions under the streets. Embodiments of the invention minimize the impact of accumulation of charge on the streets by making them small.

As shown in FIG. 2A, the first side 201 of the radiation detector 120 may include an array of discrete anode electrodes 128 comprised of an electrically conductive material, with gaps 129 between adjacent anode electrodes 128. Each anode electrode 128 may define a separate detector element (i.e., a pixel 126) of the radiation detector 120. As discussed above, a detector circuit, such as an application specific integrated circuit (ASIC) 125 shown in FIG. 1, may be coupled to the anode electrodes 128 and may be configured to read out electric signals (e.g., charge or current) for each pixel 126 of the radiation detector 120. The gaps 129 between the adjacent anode electrodes 128 may also be referred to as "streets" or "roads." The "streets" 129 may have a width, W, between the peripheral edges of the adjacent anode electrodes 128 between which the street 129 extends. In the embodiment shown in FIG. 2A, the streets 129 are arranged in a grid pattern, with a first plurality of streets 129 extending in a first horizontal direction hd1 and separated from one another in a second horizontal direction hd2, and a second plurality of streets 129 extending in the second horizontal direction hd2 and separated from one another in the first horizontal direction hd1, where an array of rectangularly-shaped anode electrodes 128 are located between the respective streets 129. Further, each of the streets 129 has a substantially uniform width, W. Other geometries for the anode electrodes 128 and the streets 129 are within the contemplated scope of this disclosure, including anode electrodes 128 having non-uniform and/or non-rectangular shapes (e.g., triangular, elliptical and/or irregularly shaped anodes), as well as streets 129 having non-uniform spacing and/or widths.

Referring to FIG. 2B, the second side 203 of the radiation detector 120 may include a cathode electrode 122 comprised of an electrically conductive material. In the embodiment shown in FIG. 2B, the cathode electrode 122 may be a monolithic cathode electrode, meaning that a single cathode electrode 122 extends continuously over the surface of the semiconductor material substrate 124 located opposite to the first side 201 of the radiation detector 120. Alternately, the cathode electrode 122 may include a plurality of discrete segments of conductive material over the surface of the semiconductor material substrate 124, where each segment may correspond to a subset of one or more pixels 126 of the pixel array.

For direct photon measuring radiation detectors, such as photon counting computed tomography (PCCT) detectors, an important performance specification is the stability of the photon count rate over time. Specifically, the response of the detector to a step change of photon flux, similar to what is experienced in a clinical situation, may be measured over a predetermined time duration. Ideally, the relative change in the detector response over time should be close to zero for as many pixels as possible.

One measure of PCCT detector stability may be conducted over 1 minute, or a similar time period that is selected to be roughly equivalent to the duration of a CT scan. The detector may be exposed to X-ray radiation for an exposure period (e.g., a 1 minute exposure for a 1 minute stability test). The average count rate "A" during a first portion (N1) of the exposure period may be compared to the average count rate "B" during a second, subsequent portion (N2) of the exposure period. In one embodiment, the first portion, N1, of the exposure period may be 5-20 seconds, such as 10-15 seconds, in duration, and may begin concurrently with, or shortly (e.g., within 5 seconds) after the beginning of the exposure period. The second portion, N2, of the exposure period may be 5-20 seconds, such as 10-15 seconds, in duration, and may occur at or near the end of the exposure period. In one embodiment, the count rate stability, CRS, may be measured as (A−B)/B (i.e., CRS=(A−B)/B). In another embodiment, the count rate stability, CRS, may be measured as (A−B)/C (i.e., CRS=(A−B)/C), where "C" corresponds to the average count rate during the entire exposure period (e.g., the average count rate between zero and 60 seconds for a 1 minute stability test).

The count rate stability, CRS, may be determined for each pixel of the radiation detector and compared to a threshold value, such as 0.1% to 1%. Any pixel whose CRS value exceeds the threshold value may be considered a Non-Conforming Pixel (NCP). The resulting number of NCPs as a fraction of the total number of pixels in the detector is an indication of detector performance, where lower NCPs is better. In some embodiments, the number of NCPs during a stability test should be less than a predetermined number (e.g., maximum allowable number) of the total pixels in the detector.

Referring again to FIGS. 1 and 2A, various embodiments of the present disclosure include photon counting radiation detectors 120, such as photon counting computed tomography (PCCT) detectors, having reduced street widths, W, between adjacent anode electrodes 128, such as street widths that are less than 15 μm. In embodiments, the street widths of the radiation detector 120 may be between 0.1 μm and 14 μm (e.g., 1 μm to 12 μm), including between 5 μm and 10 μm. A photon counting radiation detector with reduced street widths according to various embodiments may have improved count rate stability (CRS) characteristics and a reduced number of Non-Conforming Pixels (NCPs) relative to conventional radiation detectors with wider street width.

Conventional PCCT radiation detectors typically have street widths on the order of 35 μm to 75 μm. One reason for this is because decreasing the distance between adjacent anode electrodes increases the capacitive coupling between the anodes. Increasing the capacitive coupling between anodes is generally understood as having a negative effect on the photon count signal accuracy as well as increasing the effective input noise of the detector. However, the present inventors have realized that any negative impact of a small (e.g., <15 μm) street width is more than offset by the improvements in 1 minute stability performance and the reduction in Non-Conforming Pixels (NCPs). Furthermore, by connecting the anode electrodes to charge sensitive amplifier (CSA) inputs within the ASICs, the impact of increasing inter-pixel capacitance may be mitigated. In various embodiments, the CSA is a feedback amplifier whose input terminal behaves like a virtual ground, and because of the feedback configuration the input terminal is maintained at a substantially constant voltage. In this situation, capacitive coupling from an adjacent anode to a neighbor is zero to a first order because any current flowing into the CSA input generates a small voltage on the anode terminal. The capacitive coupling current i(t) is given by i(t)=C(dV/dt), where C is the coupling capacitance and V is the voltage between the two anodes. Since dV is small, therefore the current i(t) is also small, even if the coupling capacitance C is non-zero.

Figure 3:
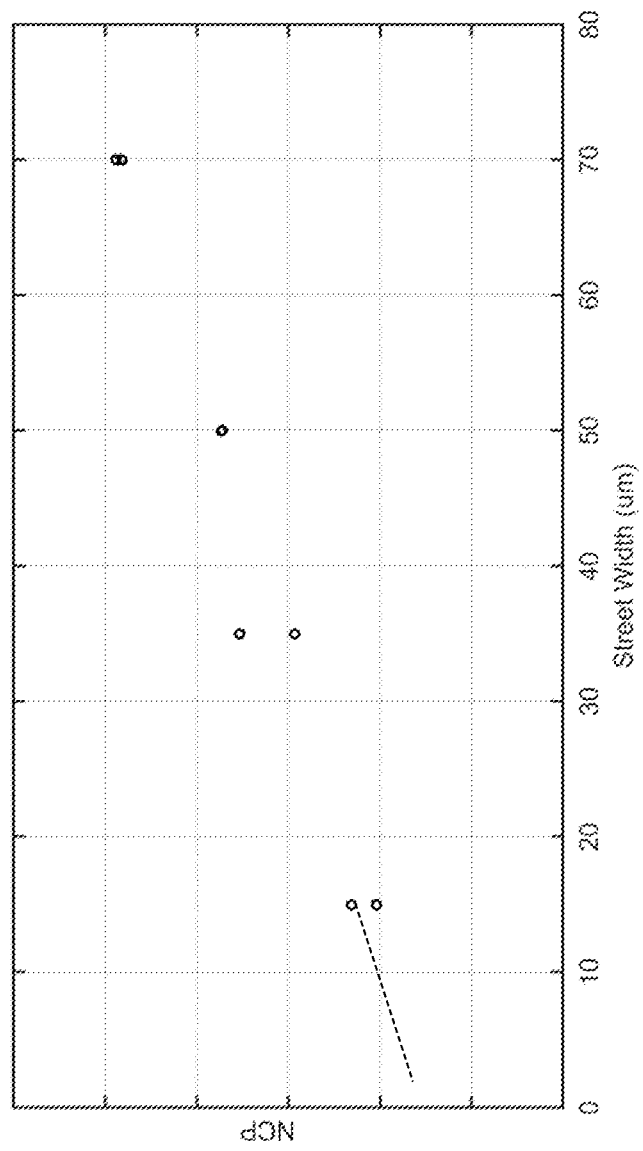
FIG. 3 is a plot of the number of non-conforming pixels versus street width for 1 minute stability determination of an ionizing radiation detector, according to various embodiments of the present disclosure.

FIG. 3 is a plot of the number of non-conforming pixels (in arbitrary units) of PCCT radiation detectors 120 versus street width for a 1 minute stability determination. There are two detectors at each of the street widths shown in FIG. 3 (the data from the two detectors at 50 micron street width overlap in this figure). Each of the radiation detectors 120 included the same number of pixels and substantially identical construction but with street widths of 70 μm, 50 μm, 35 μm and 15 μm. As shown in FIG. 3, the number of Non-Conforming Pixels (NCP) of the radiation detectors 120 decreased as a function of decreasing street width. The dashed line in FIG. 3 is an extrapolation based on the test data trend illustrating the expected decrease in NCP values as the street width is reduced beyond 15 μm.

In embodiments, a radiation detector having street widths less than 15 μm may have a reduction in NCPs from a 1 minute stability determination that is ≥25%, such as ≥33%, including ≥40% or ≥50%, relative to the NCPs from a 1 minute stability determination of an otherwise equivalent radiation detector having street widths of 35 μm.

According to one embodiment illustrated in FIGS. 2A-2C, an ionizing radiation detector 120 includes a semiconductor material plate 124, a plurality of anodes 128 located on a first side 201 (e.g., first surface) of the semiconductor material plate 124, where the gaps 129 between adjacent anodes 128 are less than 15 μm in width, and at least one cathode 122 located on a second side 203 (e.g., second surface) of the semiconductor material plate 124.

In one embodiment, the ionizing radiation detector 120 is a photon counting computed tomography detector. In one embodiment, the semiconductor material plate 124 is a cadmium zinc telluride semiconductor material plate. In one embodiment, the width of the gaps 129 between adjacent anodes 128 are between 0.1 μm and 14 μm, such as between 5 μm and 10 μm.

In one embodiment, the ionizing radiation detector 120 includes a plurality of detector pixels 126, and each detector pixel 126 contains one anode 128. In one embodiment, the at least one cathode 122 is a single cathode located on the second side 203 of the semiconductor material plate 124 that extends over all of the detector pixels 126 of the ionizing radiation detector 120.

In one embodiment shown in FIG. 2C, the ionizing radiation detector 120 includes a passivation layer 403 located within the gaps 129 between adjacent anodes 128 on the first side 201 of the semiconductor material plate 124. In one embodiment, the passivation layer 403 extends beneath the anodes 128 on the first side 201 of the semiconductor material plate 124. Another passivation layer 404 may be located on the second side 203 of the semiconductor material plane 124 below the cathode 122.

In one embodiment, the ionizing radiation detector 120 has at least 25% less non-conforming pixels from a 1 minute count rate stability measurement than an equivalent ionizing radiation detector in which the gaps 129 between adjacent anodes 128 are 35 μm.

In one embodiment, the ionizing radiation detector 120 includes a read-out integrated circuit 125 having charge sensitive amplifier inputs connected to respective anodes 128 of the plurality of anodes.

According to another embodiment illustrated in FIGS. 1 and 2A-2C, a photon counting computed tomography imaging system 100 includes an ionizing radiation detector 120, an X-ray source 110 configured to emit an X-ray beam 135 towards the ionizing radiation detector 120 and an object 10 located between the X-ray source 110 and the ionizing radiation detector 120, and a control unit 170 configured to control the operation of the X-ray source 110 and the ionizing radiation detector 120 to obtain images of the object 10. The ionizing radiation detector 120 includes a semiconductor material plate 124, a plurality of anodes 128 located on a first side 201 of the semiconductor material plate 124, where the gaps 129 between adjacent anodes 128 are less than 15 μm in width, and at least one cathode 122 located on a second side 203 of the semiconductor material plate 124.

In one embodiment, the photon counting computed tomography system 110 additionally includes a high voltage bias power supply 130 coupled to the ionizing radiation detector 120 and configured to generate an electric field in the semiconductor material plate 124, a read-out circuit 125 coupled to the plurality of anodes 128 and configured to receive electrical signals from each of the anodes 128, and 160 a processor coupled to the read-out circuit 125 and configured to generate images of the object 10 based on the electrical signals received from the read-out circuit 125.

The present embodiments may be implemented in systems used for medical imaging, such as CT imaging, as well as for non-medical imaging applications, such as industrial inspection applications.

While the disclosure has been described in terms of specific embodiments, it is evident in view of the foregoing description that numerous alternatives, modifications and variations will be apparent to those skilled in the art. Each of the embodiments described herein may be implemented individually or in combination with any other embodiment unless expressly stated otherwise or clearly incompatible. Accordingly, the disclosure is intended to encompass all such alternatives, modifications and variations which fall within the scope and spirit of the disclosure and the following claims.

What is claimed is:

1. An ionizing radiation detector, comprising:
a semiconductor material plate;
a plurality of anodes located on a first side of the semiconductor material plate, wherein gaps between adjacent anodes of the plurality of anodes are less than 15 μm in width; and
at least one cathode located on a second side of the semiconductor material plate.

2. The ionizing radiation detector of claim 1, wherein the ionizing radiation detector comprises a photon counting computed tomography detector.

3. A photon counting computed tomography imaging system, comprising:
the ionizing radiation detector of claim 2;
an X-ray source configured to emit an X-ray beam towards the ionizing radiation detector and an object located between the X-ray source and the ionizing radiation detector; and
a control unit configured to control the operation of the X-ray source and the ionizing radiation detector to obtain images of the object.

4. The photon counting computed tomography system of claim 3, further comprising:
a high voltage bias power supply coupled to the ionizing radiation detector and configured to generate an electric field in the semiconductor material plate;
a read-out circuit coupled to the plurality of anodes and configured to receive electrical signals from each of the anodes; and
a processor coupled to the read-out circuit and configured to generate images of the object based on the electrical signals received from the read-out circuit.

5. The ionizing radiation detector of claim 1, wherein the semiconductor material plate comprises a cadmium zinc telluride semiconductor material plate.

6. The ionizing radiation detector of claim 1, wherein the width of the gaps between adjacent anodes of the plurality of anodes are between 0.1 μm and 14 μm.

7. The ionizing radiation detector of claim 4, wherein the width of the gaps between adjacent anodes of the plurality of anodes are between 5 μm and 10 μm.

8. The ionizing radiation detector of claim 1, wherein the ionizing radiation detector comprises a plurality of detector pixels and each detector pixel contains one anode of the plurality of anodes.

9. The ionizing radiation detector of claim 6, wherein the at least one cathode comprises a single cathode located on the second side of the semiconductor material plate, and the cathode extends over all of the detector pixels of the ionizing radiation detector.

10. The ionizing radiation detector of claim 6, wherein the ionizing radiation detector has at least 25% less non-conforming pixels from a 1 minute count rate stability measurement than an equivalent ionizing radiation detector in which the gaps between adjacent anodes are 35 μm.

11. The ionizing radiation detector of claim 1, further comprising a passivation layer located within the gaps between adjacent anodes of the plurality of anodes on the first side of the semiconductor material plate.

12. The ionizing radiation detector of claim 8, wherein the passivation layer extends beneath the plurality of anodes on the first side of the semiconductor material plate.

13. The ionizing radiation detector of claim 1, further comprising a read-out integrated circuit having charge sensitive amplifier inputs connected to respective anodes of the plurality of anodes.

* * * * *